(12) United States Patent
He et al.

(10) Patent No.: US 11,497,529 B2
(45) Date of Patent: Nov. 15, 2022

(54) ORTHOPEDICS RESTORATION FIXATION DEVICE (71) Applicants: HEFEI BOE OPTOELECTRONICS TECHNOLOGY CO., LTD., Hefei (CN); BOE TECHNOLOGY GROUP CO., LTD., Beijing (CN)

(72) Inventors: Panpan He, Beijing (CN); Yan Wang, Beijing (CN)

(73) Assignees: HEFEI BOE OPTOELECTRONICS TECHNOLOGY CO., LTD., Anhui (CN); BEIJING BOE TECHNOLOGY DEVELOPMENT CO., LTD., Beijing (CN)

( * ) Notice: Subject to any disclaimer, the term of this patent is extended or adjusted under 35 U.S.C. 154(b) by 287 days.

(21) Appl. No.: 16/509,323

(22) Filed: Jul. 11, 2019

(65) Prior Publication Data
US 2020/0129208 A1  Apr. 30, 2020

(30) Foreign Application Priority Data

Oct. 29, 2018 (CN) .......................... 201811270239.5

(51) Int. Cl.
*A61F 5/00* (2006.01)
*A61B 17/66* (2006.01)
*A61B 17/62* (2006.01)
*A61F 5/01* (2006.01)
*A61F 5/04* (2006.01)
(Continued)

(52) U.S. Cl.
CPC .............. *A61B 17/66* (2013.01); *A61B 17/62* (2013.01); *A61F 5/01* (2013.01); *A61F 5/04* (2013.01); *A61B 17/6458* (2013.01); *A61B 17/6466* (2013.01); *A61B 2017/564* (2013.01); *A61B 2017/606* (2013.01)

(58) Field of Classification Search
CPC ......... A61B 17/56; A61B 17/66; A61B 17/62; A61B 17/6458; A61B 17/6466; A61B 2017/564; A61B 2017/606; A61F 5/01; A61F 5/04
USPC ........................................................... 602/32
See application file for complete search history.

(56) References Cited

U.S. PATENT DOCUMENTS

2017/0014975 A1 * 1/2017 Edge ....................... B25B 5/006

FOREIGN PATENT DOCUMENTS

CN  103151478 A * 6/2013
CN  204181636 U   3/2015
(Continued)

OTHER PUBLICATIONS

First Chinese Office Action dated Apr. 26, 2020, received for corresponding Chinese Application No. 201811270239.5, 26 pages.

*Primary Examiner* — Alireza Nia
*Assistant Examiner* — Michael Milo
(74) *Attorney, Agent, or Firm* — Kinney & Lange, P.A.

(57) ABSTRACT

An orthopedics restoration fixation device includes: a clamping mechanism and a shock absorbing mechanism. The clamping mechanism includes: a first base; a first clamping assembly and a second clamping assembly cooperating with each other and adjustably mounted on the first base; and an adjustment assembly mounted on the first base and configured to move the first clamping assembly and the second clamping assembly towards each other or away from each other. The shock absorbing mechanism is connected to the clamping mechanism and is configured to alleviate an external impact on the clamping mechanism.

15 Claims, 4 Drawing Sheets

(51) Int. Cl.
   *A61B 17/64* (2006.01)
   *A61B 17/56* (2006.01)
   *A61B 17/60* (2006.01)

(56) References Cited

FOREIGN PATENT DOCUMENTS

| | | | | |
|---|---|---|---|---|
| CN | 204293325 | U | | 4/2015 |
| CN | 204293325 | U | * | 4/2015 |
| CN | 104586481 | A | * | 5/2015 |
| CN | 204542512 | U | | 8/2015 |
| CN | 105012006 | A | * | 11/2015 |
| CN | 105310757 | A | * | 2/2016 |
| CN | 105748136 | A | * | 7/2016 |
| CN | 105877834 | A | * | 8/2016 |
| CN | 206135258 | U | * | 4/2017 |
| CN | 206239670 | U | | 6/2017 |
| CN | 206275791 | U | * | 6/2017 |
| CN | 206275791 | U | | 6/2017 |
| CN | 107432769 | A | | 12/2017 |
| CN | 107432781 | A | | 12/2017 |
| CN | 207011855 | U | | 2/2018 |
| CN | 207011855 | U | * | 2/2018 |
| CN | 108076768 | A | | 5/2018 |
| CN | 108076768 | A | * | 5/2018 |
| CN | 108143528 | A | | 6/2018 |
| CN | 108187195 | A | | 6/2018 |
| CN | 108257456 | A | * | 7/2018 ............ B43L 21/00 |
| CN | 108257456 | A | | 7/2018 |
| CN | 108263599 | A | | 7/2018 |
| CN | 207613938 | A | | 7/2018 |
| CN | 207613938 | U | * | 7/2018 |
| CN | 207640547 | U | | 7/2018 |
| CN | 1108263599 | A | | 7/2018 |
| CN | 108403184 | A | * | 8/2018 ......... A61B 17/1635 |
| CN | 207707997 | U | | 8/2018 |
| CN | 207768692 | U | | 8/2018 |
| CN | 108553246 | A | | 9/2018 |
| CN | 108553246 | A | * | 9/2018 ............ A61F 15/00 |
| CN | 108656485 | A | | 10/2018 |
| CN | 207949908 | U | | 10/2018 |
| CN | 207979695 | U | | 10/2018 |

* cited by examiner

ORTHOPEDICS RESTORATION FIXATION DEVICE

CROSS-REFERENCE TO RELATED APPLICATION

This application claims priority to Chinese Patent Application No. 201811270239.5 filed on Oct. 29, 2018 in the State Intellectual Property Office of China, the disclosure of which is hereby incorporated by reference in its entirety.

TECHNICAL FIELD

The present disclosure relates to the field of medical apparatus and instruments, and particularly, to an orthopedics restoration fixation device.

BACKGROUND

In the treatment of orthopedic injuries, it is usually necessary to fix the fracture site with a fixation device to consolidate the restoration effect and promote the healing speed and quality of the fracture site.

At present, some orthopedic fixation devices have a good fixation effect, but their structures are complicated, the operations are inconvenient, the installations and uninstallations are troublesome, time-consuming and labor-intensive, and they cannot be used for fixing different parts. Some other orthopedic fixation devices are simple in structure but have poor fixation effect. In addition, the conventional orthopedic fixation devices usually do not have a shock absorbing effect, and the pain is obvious when the patient turns over and moves, moreover, it is inconvenient to adjust the height, resulting in inconvenience in use.

SUMMARY

According to an aspect of the present disclosure, there is provided an orthopedics restoration fixation device comprising a clamping mechanism and a shock absorbing mechanism. The clamping mechanism comprises: a first base; a first clamping assembly and a second clamping assembly cooperating with each other and adjustably mounted on the first base; and an adjustment assembly mounted on the first base and configured to move the first clamping assembly and the second clamping assembly towards each other or away from each other. The shock absorbing mechanism is connected to the clamping mechanism and is configured to alleviate an external impact on the clamping mechanism.

In some embodiments, the adjustment assembly comprises: a first adjustment member fixedly connected to the first clamping assembly; a second adjustment member fixedly connected to the second clamping assembly; and an operation sub-assembly being in a drive connection with the first adjustment member and the second adjustment member, respectively, so that the operation sub-assembly drives, by the first adjustment member and the second adjustment member, respectively, the first clamping assembly and the second clamping assembly to move towards each other or away from each other.

In some embodiments, the first adjustment member comprises a first screw rod; the second adjustment member comprises a second screw rod; the operation sub-assembly comprises a first rotation shaft rotatably provided on the first base; and a first bevel gear and an operation part are respectively provided at two ends of the first rotation shaft, the first screw rod and the second screw rod are coaxially provided, a second bevel gear and a third bevel gear are respectively provided at ends of the first screw rod and the second screw rod facing towards each other, and the first bevel gear is engaged respectively with the second bevel gear and the third bevel gear.

In some embodiments, the first clamping assembly comprises: a first clamping member; and a first support member connected to the first clamping member and movably provided on the first base; and the second clamping assembly comprises: a second clamping member provided opposite to the first clamping member; and a second support member connected to the second clamping member and movably provided on the first base.

In some embodiments, the first clamping member and the second clamping member are arc-shaped clamping members, and concave surfaces of the first clamping member and the second clamping member face towards each other and are respectively provided with a first anti-slip mat and a second anti-slip pad.

In some embodiments, the shock absorbing mechanism comprises a second base and a third base provided opposite to each other but being able to move towards each other or away from each other; the second base is connected to the first base, the third base is located at a side of the second base away from the first base, and at least one elastic sub-assembly is provided between the second base and the third base; and a relative movement direction between the second base and the third base is substantially perpendicular to a relative movement direction between the first clamping assembly and the second clamping assembly.

In some embodiments, the elastic sub-assembly comprises: an elastic ball and a plurality of elastic strips that are arranged such that: the plurality of elastic strips collectively surround the elastic ball, and two ends of each of the plurality of elastic strips are respectively connected to the second base and the third base, so that the plurality of elastic strips are configured to be bent and pressed against the elastic ball when the second base and the third base move towards each other.

In some embodiments, first springs are provided respectively between the elastic ball and the second base and between the elastic ball and the third base.

In some embodiments, each of the first springs is provided within a guide sleeve of which one end is fixedly connected to the second base or the third base and the other end is close to the elastic ball.

In some embodiments, a plurality of said elastic sub-assemblies are provided at intervals between the second base and the third base; each of the elastic sub-assemblies comprises: one said elastic ball, and two said elastic strips opposite to each other; and one of the two said elastic strips in one of adjacent ones of said elastic sub-assemblies and one, adjacent to the one of the two said elastic strips in the one of the adjacent said elastic sub-assemblies, of the two said elastic strips in the other of the adjacent ones of said elastic sub-assemblies are abutted against each other after bent, to restrict a further bending of the two said elastic strips.

In some embodiments, a first sleeve is provided on one of the second base and the third base, a positioning rod is provided on the other one of the second base and the third base, and the positioning rod is provided to pass through the first sleeve and be movable in an axial direction of the first sleeve.

In some embodiments, a second spring is sleeved on the positioning rod, and has two ends respectively abutted against the other one of the second base and the third base and the first sleeve.

In some embodiments, the clamping mechanism is detachably connected to the shock absorbing mechanism.

In some embodiments, a block is provided on the first base, a groove is formed in the shock absorbing mechanism, and the block is configured to be fitted into the groove by rotation.

In some embodiments, the orthopedics restoration fixation device further comprises: a distance adjusting mechanism connected to the shock absorbing mechanism and also connected with the clamping mechanism via the shock absorbing mechanism, and configured to adjust a distance between the shock absorbing mechanism and the clamping mechanism.

In some embodiments, the distance adjusting mechanism comprises: a fourth base provided with at least one inclined guide rail; a bracket movably connected between the fourth base and the shock absorbing mechanism; a third screw rod provided on the bracket; and a slider threadedly connected to the third screw rod and slidably supported to the inclined guide rail, so that the bracket moves when the slider is driven by the third screw rod to move along the inclined guide rail.

In some embodiments, the bracket comprises: a supporting rod, and a second sleeve provided on the fourth base; and the supporting rod has one end connected to the shock absorbing mechanism and the other end retractably connected in the second sleeve, so that the shock absorbing mechanism is movable relative to the fourth base.

In some embodiments, the orthopedics restoration fixation device further comprises an anti-slip mat layer provided between the supporting rod and the second sleeve.

In some embodiments, the orthopedics restoration fixation device further comprises a positioning roll provided at one end of the slider and abutted against the inclined guide rail.

It should be understood that, the above general description and the following detailed description are to be considered as exemplary and illustrative, rather than limiting the present disclosure.

This section provides an overview of various implementations or examples of the technical solutions described in the present disclosure, and it is not a comprehensive description of the full scope or all features of the technical solutions described in the present disclosure.

BRIEF DESCRIPTION OF THE DRAWINGS

In order to more clearly illustrate the technical solutions according to the embodiments of the present disclosure, the drawings for the embodiments will be briefly described below. It is obvious that the drawings in the following description relate only to some embodiments of the present disclosure, and are not to limit the present disclosure.

DETAILED DESCRIPTION OF THE EMBODIMENTS

In order to make the objects, technical solutions and advantages of the embodiments of the present disclosure more clear, technical solutions of the embodiments of the present disclosure will be clearly and completely described below in conjunction with the drawings of the embodiments of the present disclosure. It is apparent that the described embodiments are some of the embodiments of the present disclosure, and not all of the embodiments. All other embodiments obtained by those skilled in the art based on the described embodiments of the present disclosure without involving inventive labors are within the protective scope of the present disclosure.

Unless otherwise defined, technical terms or scientific terms used in the present disclosure are intended to be ordinary meanings understood by those skilled in the art. The words "first", "second", and similar terms used in the present disclosure do not denote any order, quantity, or importance, but are used to distinguish different elements/components. The word "comprise", "comprising" or the like means that the element or part preceding the word is intended to cover the element(s) or the item(s) and its equivalents that are listed after the word, and do not exclude other element(s) or item(s).

Spatially related terms, including but not limited to, "below," "above," "on bottom," and "on top," if used herein, are utilized for ease of description to describe spatial relationships of an element(s) to another. Such spatially related terms encompass different orientations of the device in use or operation in addition to the particular orientations depicted in the figures and described herein. For example, if an object depicted in the figures is turned over or flipped over, portions previously described as below or beneath other elements would then be above those other elements.

In order to keep the following description of the embodiments of the present disclosure clear and concise, the present disclosure omits detailed descriptions of well-known functions and well-known components/elements.

Figure 1:
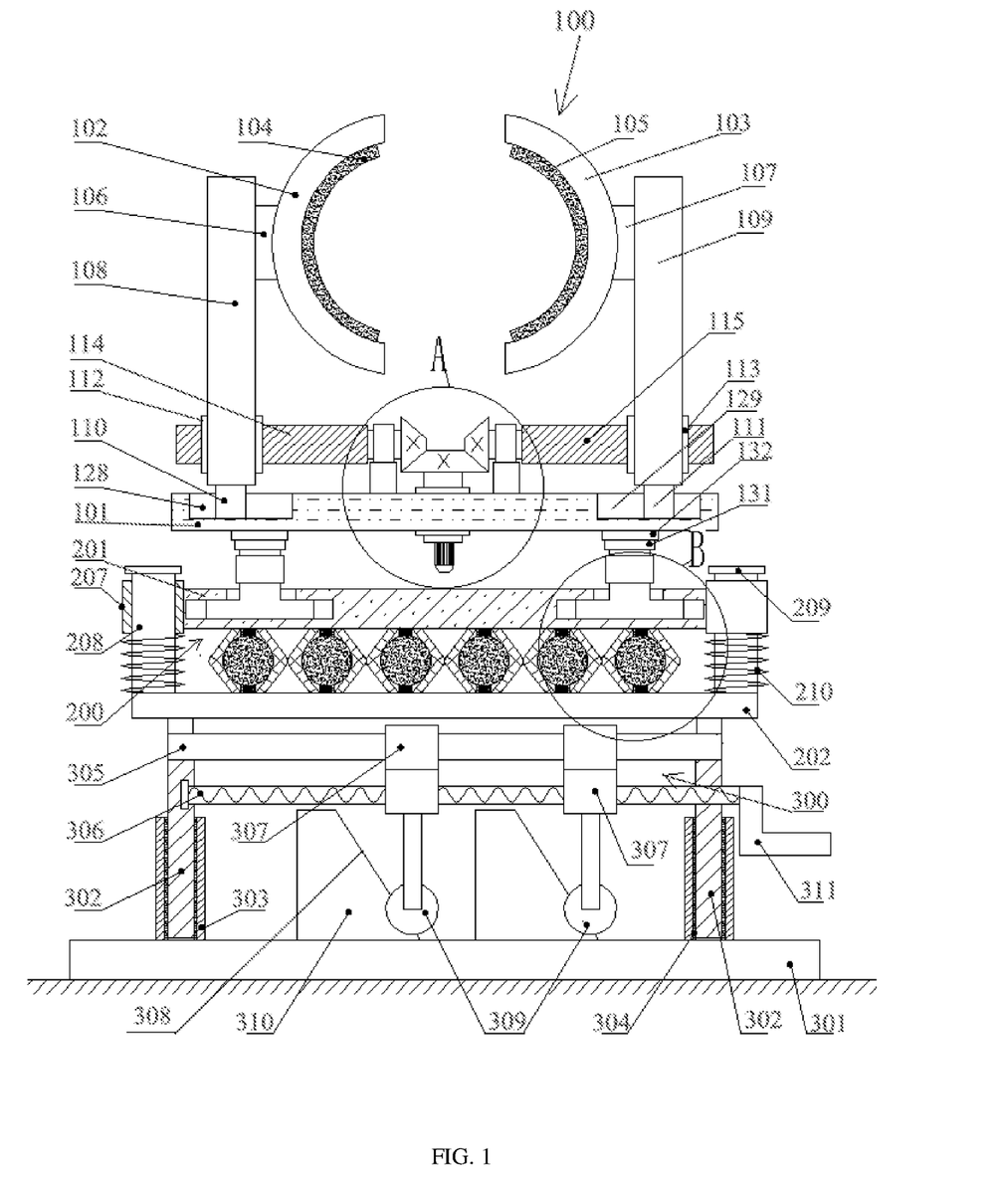
FIG. 1 is a schematic view showing a structure of an orthopedics restoration fixation device according to an embodiment of the present disclosure.

FIG. 1 is a schematic view showing a structure of an orthopedics restoration fixation device according to an embodiment of the present disclosure. Referring to FIG. 1, the orthopedics restoration fixation device comprises a clamping mechanism 100 and a shock absorbing mechanism 200. The clamping mechanism 100 comprises a first base 101, and a first clamping assembly, a second clamping assembly, and an adjustment assembly mounted on the first base 101. When in use, the medical staff can use the adjustment assembly to drive the first clamping assembly and the second clamping assembly to move towards each other so as to clamp the patient's fracture site, or use the adjustment assembly to drive the first clamping assembly and the second clamping assembly to move away from each other so as to remove it from the patient's fracture site. With the above configuration, the fixation device is simple in structure and convenient in operation, and is beneficial for reducing the operation difficulty of the medical staff and shortening the operation time of the medical staff. At the same time, in the orthopedics restoration fixation device according to embodiments of the present disclosure, a shock absorbing mechanism 200 is connected to the clamping mechanism 100 (in FIG. 1, the shock absorbing mechanism 200 is disposed at the bottom of the clamping mechanism 100) for alleviating an external impact on the clamping mechanism. Thereby, the impact force between the patient's fracture site and the clamping mechanism 100 can be absorbed, and the pain of the patient when moving relative to the clamping mechanism 100 such as turning over or moving the body can be alleviated, improving the patient's comfort.

In some embodiments, as shown in FIG. 1, the first clamping assembly comprises a first clamping member 102 and a first support member 108. The first clamping member 102 can be connected to the first support member 108 via a first fixation piece 106, alternatively, the first clamping member 102 can also be connected directly to the first support member 108. The first support member 108 has a first sliding part 110 at its bottom and the first base 101 has a first sliding groove 128 at its top. The first sliding part 110 is movably disposed in the first sliding groove 128. The second clamping assembly comprises a second clamping member 103 and a second support member 109. The second support member 109 and the first support member 108 are disposed opposite to each other, and the first clamping member 102 and the second clamping member 103 are disposed opposite to each other. The second clamping member 103 can be connected to the second support member 109 via a second fixation piece 107, alternatively, the second clamping member 103 can also be connected directly to the second support member 109. The second support member 109 has a second sliding part 111 at its bottom and the first base 101 further has a second sliding groove 129 at its top. The second sliding part 111 is movably disposed in the second sliding groove 129. The first sliding groove 128 and the second sliding groove 129 are oriented in a same linear direction. With this configuration, when driven by the adjustment assembly, the first support member 108 is movable along the first sliding groove 128 by the first sliding part 110, and the second support member 109 is movable along the second sliding groove 129 by the second sliding part 111. The movement process is smooth and stable.

In some embodiments, as shown in FIG. 1, the first clamping member 102 and the second clamping member 103 both can be arc-shaped clamping members, and concave surfaces of the first clamping member 102 and the second clamping member 103 face towards each other and are respectively provided with a first anti-slip mat 104 and a second anti-slip pad 105. The first anti-slip mat 104 and the second anti-slip pad 105 may be rubber mats or other anti-slip mats made of flexible materials, so that the comfort of the patient's fracture site is improved, and the fracture site is not easily out of the anti-slip mats between the first clamping member 102 and the second clamping member 103. The structure is compact, the design is reasonable, and the practicality is strong. In addition, the width of each of the first clamping member 102 and the second clamping member 103 in the present embodiment is set to be 20 cm to 22 cm.

Of course, specific structure of the first clamping assembly, specific structure of the second clamping assembly, and specific structure of the connection between the first clamping assembly, the second clamping assembly and the first base 101 are not limited to the above configurations, and the clamping mechanism according to the present disclosure can adopt any configuration that achieves clamping and fixing effects as well as ease of operation (e.g., clamping operation and removal operation).

In some embodiments, the adjustment assembly comprises: a first adjustment member fixedly connected to the first clamping assembly; a second adjustment member fixedly connected to the second clamping assembly; and an operation sub-assembly being in a drive connection with the first adjustment member and the second adjustment member, respectively, so that the operation sub-assembly drives, by the first adjustment member and the second adjustment member, respectively, the first clamping assembly and the second clamping assembly to move towards each other or away from each other. Specifically, in the embodiment show in FIG. 1, the adjustment assembly can comprise: a first screw rod 114; a second screw rod 115; and the operation sub-assembly. The first screw rod 114 and the second screw rod 115 are arranged opposite to each other. In the present embodiment, the first screw rod 114 and the second screw rod 115 are disposed coaxially at the top of the first base 101. A first nut 112 and a second nut 113 are fixedly connected to the first support member 108 and the second support member 109, respectively, and the first nut 112 and the second nut 113 are threaded connected to the first screw rod 114 and the second screw rod 115, respectively. The operation sub-assembly is in a drive connection with both the first screw rod 114 and the second screw rod 115. The operation sub-assembly drives the first screw rod 114 and the second screw rod 115 to rotate in opposite directions, to bring the first support member 108 and the second support member 109 to move towards each other or away from each other. The screw nut pair has a self-locking function, and it is not necessary to provide a locking mechanism. It is not easily loosen after the medical staff adjusts the degree of locking of these members. Of course, other mechanisms may be employed to drive the first support member 108 and the second support member 109 to move, such as a rack and pinion mechanism, an electric push rod, or other structure.

Figure 2:
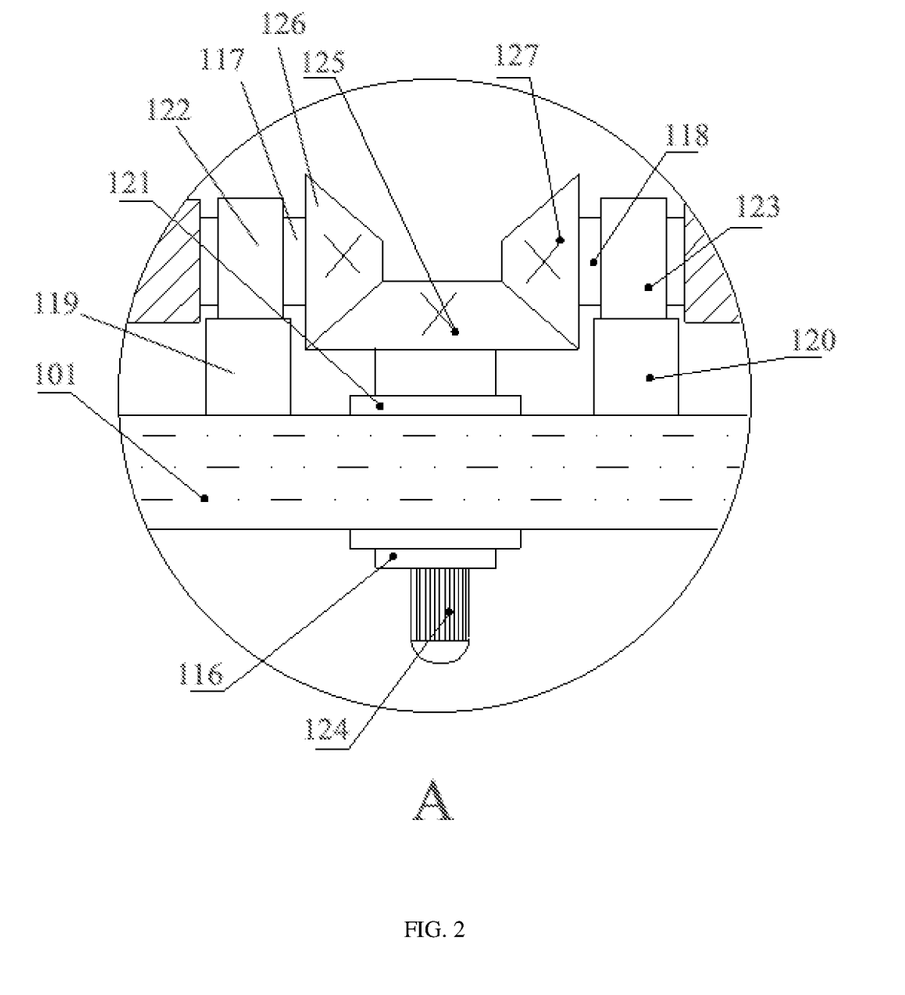
FIG. 2 is a partial enlarged view of a section A shown in FIG. 1.

Referring to FIG. 1 and FIG. 2, the operation sub-assembly can comprise a first rotation shaft 116 rotatably provided on the first base 101 via a first bearing 121; and a first bevel gear 125 and an operation part 124 are respectively provided at two ends of the first rotation shaft 116. A second rotation shaft 117 and a third rotation shaft 118 are respectively provided coaxially at ends of the first screw rod 114 and the second screw rod 115 facing towards each other. The first base 101 is provided with a first support piece 119 and a second support piece 120. The first support piece 119 and the second support piece 120 are respectively provided with a second bearing 122 and a third bearing 123. The second rotation shaft 117 is in a rotatable connection with the second bearing 122, and the third rotation shaft 118 is in a rotatable connection with the third bearing 123. Ends of the second bearing 122 and the third bearing 123 facing towards each other are respectively provided with a second bevel gear 126 and a third bevel gear 127, and the first bevel gear 125 is engaged respectively with the second bevel gear 126 and the third bevel gear 127. The first rotation shaft 116 can be rotated by the operation part 124, to bring the first bevel gear 125 to rotate. The first bevel gear 125 thus brings the first screw rod 114 and the second screw rod 115 to rotate in opposite directions by the second bevel gear 126 and the third bevel gear 127. The operation part 124 can be an operation handle manually operated by a medical staff, or can be a drive motor so that the medical staff can automatically adjust through a switch or a control system.

In some embodiments, the shock absorbing mechanism 200 comprises a second base 201 and a third base 202 provided opposite to each other. The second base 201 is close to and is connected to the first base 101, the third base 202 is located at a side of the second base 201 away from the first base 101. A shock absorbing cavity is formed between the second base 201 and the third base 202, and an elastic sub-assembly is provided in the shock absorbing cavity. The second base 201 and the third base 202 can move towards each other or away from each other, and stress can be absorbed by pressing against and deforming the elastic sub-assembly, to achieve shock absorption. For example, a relative movement direction between the second base 201 and the third base 202 of the shock absorbing mechanism 200 is substantially perpendicular to a relative movement direction between the first clamping assembly and the second clamping assembly of the clamping mechanism 100, to further achieve shock absorption.

Figure 3:
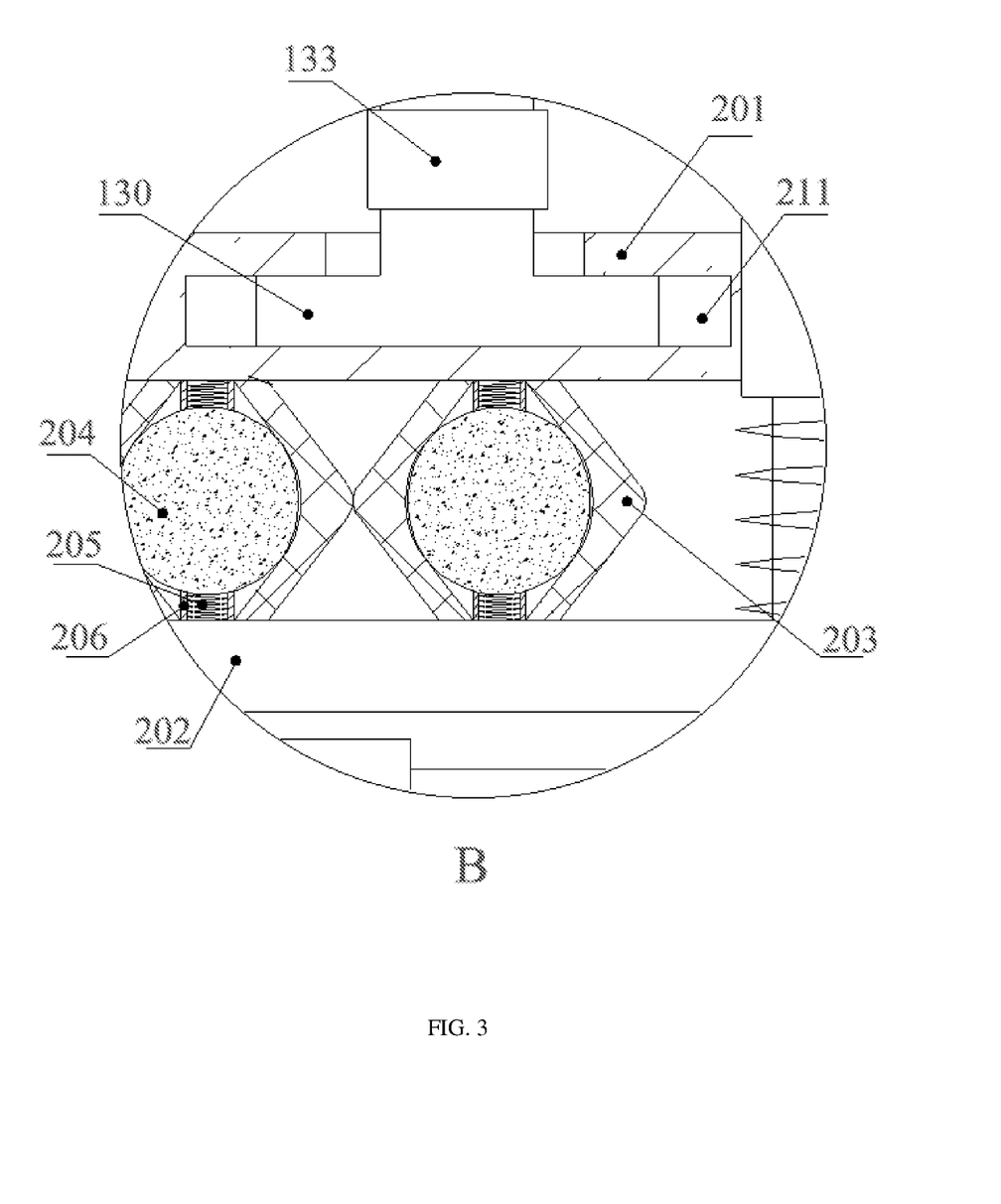
FIG. 3 is a partial enlarged view of a section B shown in FIG. 1.

Referring to FIG. 1 and FIG. 3, at least one elastic sub-assembly is provided between the second base 201 and the third base 202. Each elastic sub-assembly can comprise an elastic ball 204 and a plurality of elastic strips 203. In the present embodiment, each of the elastic sub-assemblies comprises two arc-shaped elastic strips 203, the two elastic strips 203 are disposed to face each other and form therebetween an accommodating chamber in which the elastic ball 204 is provided. That is, the two elastic strips 203 collectively surround the elastic ball 204, and two ends of each elastic strip 203 are respectively connected to the second base 201 and the third base 202. In this way, the elastic strips 203 are bent and pressed against the elastic ball 204 to deform when the second base 201 and the third base 202 move towards each other, to absorb external force. Conversely, the elastic strips 203 and the elastic ball 204 restore and release the elastic force when the external force disappears or decreases. The elastic sub-assembly has a good shock absorbing effect by cooperation of the elastic ball 204 and the elastic strips 203, and is not prone to sloshing. For example, the elastic strips 203 and the elastic ball 204 can be plastic elastic strips and plastic elastic ball, respectively.

On this basis, first springs 205 can be provided respectively between the elastic ball 204 and the second base 201 and between the elastic ball 204 and the third base 202. One ends of the two first springs 205 are fixed to the second base 201 and the third base 202, respectively. In this way, deformation of the first spring 205 itself can absorb the external force, and the two first springs 205 can also jointly press the elastic ball 204 to conduct the force, to further improve the shock absorbing effect of the elastic sub-assembly.

In addition, the two first springs 205 may be provided respectively within two guide sleeves 206. One ends of the two guide sleeves 206 are fixedly connected to the second base 201 and the third base 202, respectively, and the other ends of the two guide sleeves 206 are close to the elastic ball 204 but have a clearance with the elastic ball 204. The deformation direction of the first spring 205 can be restricted by the guide sleeve 206, so that the first spring 205 deforms along the axial direction of the guide sleeve 206. In addition, the guide sleeve 206 can also limit the amount of deformation of the first spring 205 to avoid occurrence of plastic deformation of the first spring 205.

Specifically, in the present embodiment, a plurality of elastic sub-assemblies are provided at intervals one by one in the shock absorbing cavity. One elastic strip 203 in one of adjacent ones of the elastic sub-assemblies and one elastic strip 203, adjacent to the one elastic strip 203 in the one of the adjacent elastic sub-assemblies, in the other of the adjacent ones of the elastic sub-assemblies are abutted against each other after bent, to restrict a further bending of the elastic strips 203. By adjusting the separation distance between two adjacent elastic sub-assemblies, the compressible amplitude of the elastic sub-assembly can be adjusted, thereby adjusting the shock absorbing effect of the shock absorbing mechanism 200.

In some embodiments, a first sleeve 207 is provided on one of the second base 201 and the third base 202, a positioning rod 208 is provided on the other one of the second base 201 and the third base 202, and the positioning rod 208 is provided to pass through the first sleeve 207 and be movable in an axial direction of the first sleeve 207. In the embodiment shown in FIG. 1, the first sleeve 207 is provided on the second base 201, the positioning rod 208 is provided on the third base 202, and the positioning rod 208 is provided to pass through the first sleeve 207 and be movable in an axial direction of the first sleeve 207. In case that both the second base 201 and the third base 202 are rectangular bases, one first sleeve 207 is provided at each of four corners of the second base 201, one positioning rod 208 is provided at each of four corners of the third base 202, and the four positioning rods 208 pass through the four first sleeves 207, respectively, to allow the four positioning rods 208 to be movable in axial directions of the four first sleeves 207, respectively. In this way, the second base 201 and the third base 202 are restricted to only move towards each other or away from each other. To prevent the positioning rod 208 from coming out of the first sleeve 207, a limit element 209 can be provided at the end of the positioning rod 208. In addition, a second spring 210 can be sleeved on the positioning rod 208, and two ends of the second spring 210 respectively abut against the third base 202 and the first sleeve 207. Provision of the second spring 210 can further improve the shock absorbing effect of the shock absorbing mechanism 200. It should be noted that the connection between the second base 201 and the third base 202 is not limited to the above configuration, and the elastic sub-assembly is not limited to the above configuration. The shock absorbing mechanism according to the embodiments of the present disclosure may adopt any configuration that has the shock absorbing effect on the clamping mechanism.

In some embodiments, the clamping mechanism 100 and the shock absorbing mechanism 200 can be in a detachable connection. The clamping mechanism 100 can be removed from the shock absorbing mechanism 200 as appropriate to allow the clamping mechanism 100 to be applied at different sites. Specifically, referring to FIG. 1 and FIG. 3, in the present embodiment, two blocks 130 are symmetrically disposed at the bottom of the first base 101, and the blocks 130 each are an inverted T-shaped block having a horizontal strip-shaped snap portion and a vertical connecting portion. The top of the connecting portion of the block 130 is connected to the bottom of a fourth rotation shaft 131, and the bottom of the first base 101 is provided with a fourth bearing 132, and the top of the fourth rotation shaft 131 is rotatably connected in the fourth bearing 132. The top of the second base 201 is formed with a groove 211, and the top of the groove 211 has a cover plate on which a strip-shaped notch mating in shape with the strip-shaped snap portion of the block 130 is provided, and the strip-shaped snap portion of the block 130 can be snap-fitted into the groove 211 through the strip-shaped notch. Once the connecting portion of the block 130 is rotated to rotate and offset the strip-shaped snap portion from the strip-shaped notch, the strip-shaped snap portion of the block 130 snaps into the groove 211. When the clamping mechanism 100 needs to be detached, the connecting portion of the block 130 is rotated to realign the strip-shaped snap portion with the strip-shaped notch of the groove 211, the strip-shaped snap portion of the block 130 can be removed from the groove 211. Accordingly, it is easy to disassemble and assemble, which saves the operation time of the medical staff. In addition, in order to facilitate the operation of the medical staff, a non-slip sleeve 133 can be arranged outside the connecting portion of the block 130. It should be noted that configuration of the detachable connection between the clamping mechanism 100 and the shock absorbing mechanism 200 is not limited to the above as long as the detachable connection between the two can be achieved. In addition, specific structure between the block 130 and the groove 211 is not limited to the above configuration as long as the block 130 is rotatably connected to the bottom of the first base 101, and the groove 211 is provided at the top of the shock absorbing mechanism 200, so that the block 130 can fit into the groove 211 and can be engaged with the groove 211 after rotation.

In some embodiments, the orthopedics restoration fixation device further comprises a distance adjusting mechanism. The distance adjusting mechanism is connected to the shock absorbing mechanism and also connected with the clamping mechanism via the shock absorbing mechanism, and is configured to adjust a distance between the shock absorbing mechanism and the clamping mechanism. Specifically, referring to FIG. 1, a distance adjusting mechanism 300 configured to adjust a distance between the shock absorbing mechanism 200 and the clamping mechanism 100 is provided at the bottom of the shock absorbing mechanism 200. A height of the clamping mechanism 100 can be adjusted by operating the distance adjusting mechanism 300. In this way, the orthopedics restoration fixation device can be adapted to different application environments, and the patient's fracture site can be adjusted to a height that is both medically demanding and relatively comfortable.

Specifically, referring to FIG. 1, the distance adjusting mechanism 300 comprises: a fourth base 301, a bracket and a slider 307. The fourth base 301 is used to be placed on an external surface, such as the ground or bed. The top of the fourth base 301 is provided with an inclined guide rail 308, which is a guide rail that is inclined with respect to the support surface of the fourth base 301. In this embodiment, a trapezoidal piece 310 is disposed at the top of the fourth base 301. The trapezoidal piece 310 has a trapezoidal cross section, and the inclined guide rail 308 is formed by the inclined side surface of the trapezoidal block 310. Of course, the inclined guide rail 308 can also be formed by other structures.

Figure 4:
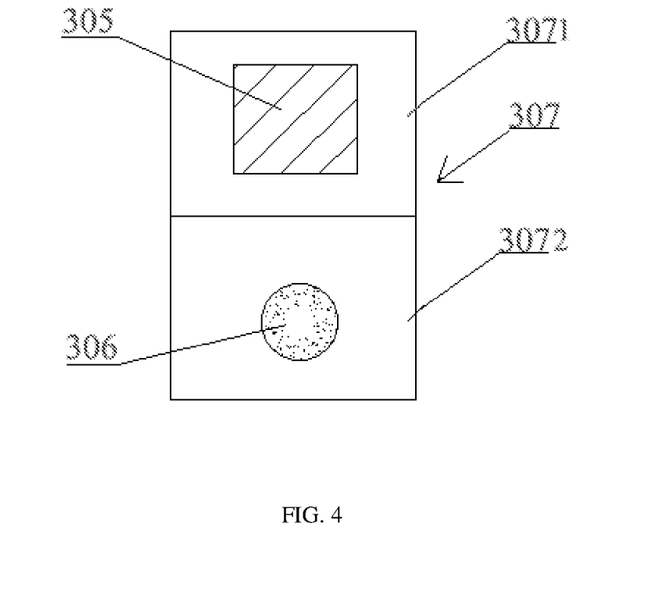
FIG. 4 is a schematic view showing a structure of a connection between a slider, a slide bar and a third screw rod in an orthopedics restoration fixation device according to an embodiment of the present disclosure.

The bracket is movably connected between the fourth base and the shock absorbing mechanism, and is configured to movably support the shock absorbing mechanism 200. As shown in FIG. 1, in this embodiment, the bracket is supported to the bottom of the third base 202 and is movably connected to the fourth base 301. A slide bar 305 and a third screw rod 306 parallel to each other are provided on the bracket. Exemplarily, the slide bar 305 and the third screw rod 306 are located on the same plane parallel to the movement direction with the inclined guide rail 308. The slide bar 305 may have a rectangular cross-sectional shape, as shown in FIG. 4. The third screw rod 306 is rotatably connected to the bracket and has one end extending from the bracket and connected to a rotating handle 311. In order to facilitate the operation of the medical staff, an anti-slip rubber sleeve can be sleeved on the rotating handle 311.

Referring to FIG. 1 and FIG. 4, the slider 307 includes a sliding connection portion 3071 having a rectangular through hole, an internal thread portion 3072 at the bottom of the sliding connection portion 3071, and a support guide portion at the bottom of the internal thread portion 3072 (for example, a positioning roll 309 which will be described later). The sliding connection portion 3071 of the slider 307 is sleeved on the slide bar 305, and the internal thread portion 9072 of the slider 307 is threaded connected to the third screw rod 306. The support guide portion of the slider 307 is supported on the inclined guide rail 308 and is movable along the inclined guide rail 308.

Once the medical staff operates the handle 311 in use, the third screw rod 306 is rotated to bring the slider 307 to move along the slide bar 305 and the inclined guide rail 308. Once the bracket is moved through the third screw rod 306 and the slide bar 305, the clamping mechanism 100 and the shock absorbing mechanism 200 will also move. Since the screw drive has a self-locking function, the slider 307 and the third screw rod 306 are self-locked after adjusting the height, thus, no locking mechanism is required, and the structure is simple and the operation is convenient.

It should be noted that, in this embodiment, the slide bar 305 is used to restrict the rotation of the slider 307 during the movement of the third screw rod 306 together with the slider 307, and, the slider 307 can bring the bracket to move by the slide bar 305. The slide bar 305 can also be replaced by providing a rail or other structure on the bracket.

In some embodiments, the bracket comprises: a supporting rod, and a second sleeve provided on the fourth base; and the supporting rod has one end connected to the shock absorbing mechanism and the other end retractably connected in the second sleeve, so that the shock absorbing mechanism is movable relative to the fourth base. Specifically, referring to FIG. 1, the bracket includes two supporting rods 302 disposed opposite to each other, and the top of the supporting rod 302 is supported at the bottom of the shock absorbing mechanism 200, more specifically, at the bottom of the third base 202 in this embodiment. The fourth base 301 is provided with a second sleeve 303 disposed along the movement direction, and the bottom of the supporting rod 302 is connected in the second sleeve 303 and is stretchable in the axial direction of the second sleeve 303. Two ends of the slide bar 305 are fixedly connected to the two supporting rods 302, respectively, and the third screw rods 306 are respectively rotatably connected to the two supporting rods 302, and are connected to the rotating handle 311 through one of the supporting rods 302. When the slider 307 moves along the inclined guide rail 308, the support rod 302 can be moved along the second sleeve 303 by the slide bar 305 and the third screw rod 306, thereby bringing the clamping mechanism 100 and the shock absorbing mechanism 200 to move. To increase the friction between the supporting rod 302 and the second sleeve 303, an anti-slip mat layer 304 can also be disposed between the supporting rod 302 and the second sleeve 303. For example, the anti-slip mat layer 304 may be fixed to the inner surface of the second sleeve 303, or to the surface of the supporting rod 302.

Figure 5:
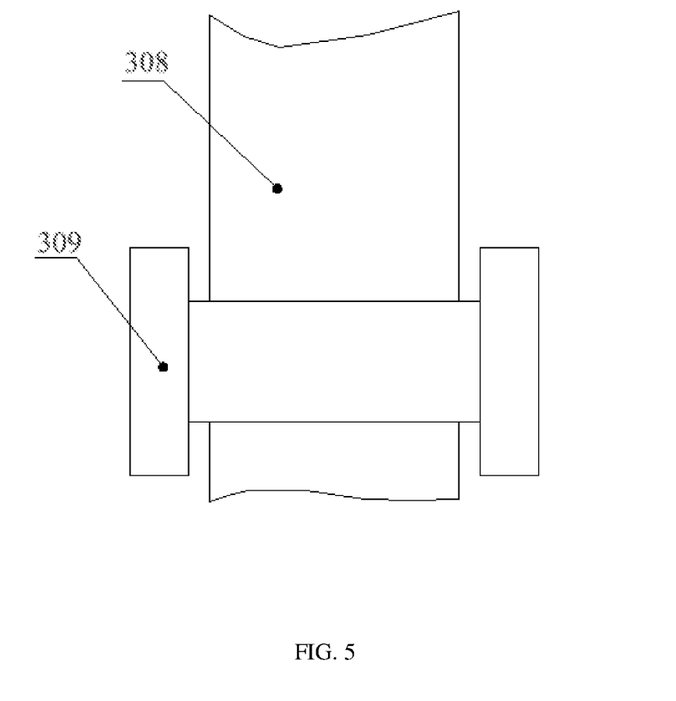
FIG. 5 is a schematic view showing a structure of a connection between a roll and an inclined guide rail in an orthopedics restoration fixation device according to an embodiment of the present disclosure.

In some embodiments, the support guide portion of the slider 307 can be formed by a positioning roll 309 disposed at the bottom of the internal thread portion of the slider 307, and the positioning roll 309 is abutted on the inclined guide rail 308, as shown in FIG. 1 and FIG. 5. The friction between the positioning roll 309 and the inclined guide rail 308 is small, and thus the positioning roll 309 can be moved relatively smoothly along the inclined guide rail 308.

In some embodiments, in order to balance the bracket during the movement process, a plurality of sliders 307 may be disposed at intervals along the axial direction of the third screw rod 306, and correspondingly, a plurality of inclined slide rails 308, in one-to-one correspondence with the plurality of sliders 307, are required to be disposed on the fourth base 301. In this embodiment, two sliders 307 are disposed at intervals, so that the third screw rod 306 can bring the two sliders 307 to move synchronously, and the two sliders 307 can synchronously and jointly bring the bracket to move in balance, preventing the occurrence of unstable movement.

Compared with the related art, the orthopedics restoration fixation device according to the embodiments of the present disclosure has at least the following advantages.

First of all, in the orthopedics restoration fixation device according to the embodiments of the present disclosure, the clamping mechanism is simple in structure, reasonable in design, and convenient in operation, and is beneficial for reducing the operation difficulty and operation time of the medical staff. Moreover, provision of the shock absorbing mechanism can absorb the impact between the patient's fracture site and the clamping mechanism, and thus the patient's pain can be alleviated to improve patient's comfort.

What's more, in the orthopedics restoration fixation device according to the embodiments of the present disclosure, the shock absorbing mechanism comprises elastic sub-assembly that is composed of elastic strips, elastic balls, first springs, and guide sleeves, and the likes, and thus achieves an improved shock absorbing effect.

In addition, in the orthopedics restoration fixation device according to the embodiments of the present disclosure, the clamping mechanism and the shock absorbing mechanism are in a detachable connection, and the clamping mechanism can be removed from the shock absorbing mechanism as needed, so that the clamping mechanism is applied in different fracture sites. In addition, the detachable connection between the two is simple in the structure, easy to disassemble and assemble, and convenient in operation.

In addition, in the orthopedics restoration fixation device according to the embodiments of the present disclosure, the distance adjusting mechanism configured to adjust a distance between the shock absorbing mechanism and the clamping mechanism is provided to the shock absorbing mechanism and the clamping mechanism. A height of the clamping mechanism can be adjusted by operating the distance adjusting mechanism 300. In this way, the orthopedics restoration fixation device can be adapted to different application environments, and the patient's fracture site can be adjusted to a height that is both medically demanding and relatively comfortable.

The above embodiments are merely exemplary embodiments of the present disclosure, and are not intended to limit the present disclosure, and the protective scope of the present disclosure is defined by the claims. Those skilled in the art can make various modifications or equivalents to the embodiments within the spirit and protective scope of the present disclosure, and such modifications or equivalents are also considered to be within the protective scope of the present disclosure.

What is claimed is:

1. An orthopedics restoration fixation device, comprising:
    a clamping mechanism, comprising:
        a first base;
        a first clamping assembly and a second clamping assembly cooperating with each other and adjustably mounted on the first base; and
        an adjustment assembly mounted on the first base and configured to move the first clamping assembly and the second clamping assembly towards each other or away from each other;
    a shock absorbing mechanism connected to the clamping mechanism and configured to alleviate an external impact on the clamping mechanism; and
    a distance adjusting mechanism connected to the shock absorbing mechanism and also connected with the clamping mechanism via the shock absorbing mechanism, and configured to adjust a distance between the shock absorbing mechanism and the clamping mechanism;
    wherein the distance adjusting mechanism comprises:
        a fourth base provided with at least one inclined guide rail;
        a bracket movably connected between the fourth base and the shock absorbing mechanism;
        a third screw rod provided on the bracket and
        a slider threadedly connected to the third screw rod and slidably supported to the inclined guide rail, so that the bracket moves when the slider is driven by the third screw rod to move along the inclined guide rail;
    wherein the bracket comprises: a supporting rod, and a second sleeve provided on the fourth base;
    wherein the supporting rod has a first end connected to the shock absorbing mechanism and a second end retractably connected in the second sleeve, so that the shock absorbing mechanism is movable relative to the fourth base;
    wherein the shock absorbing mechanism comprises a second base and a third base provided opposite to each other and being able to move towards each other or away from each other, a shock absorbing cavity is formed between the second base and the third base, a plurality of elastic sub-assemblies are provided at intervals one by one in the shock absorbing cavity, and a compressible amplitude of the elastic sub-assembly is adjusted by adjusting a separation distance between two adjacent elastic sub-assemblies;
    wherein the elastic sub-assemblies each comprise an elastic ball and a plurality of elastic strips that are arranged such that the plurality of elastic strips collectively surround the elastic ball, and opposite ends of each of the plurality of elastic strips are respectively connected to the second base and the third base, so that the plurality of elastic strips are configured to be bent and pressed against the elastic ball when the second base and the third base move towards each other; and
    wherein a first elastic strip in a first elastic sub-assembly that is adjacent to a second elastic sub-assembly, and a second elastic strip in the second elastic sub-assembly that is adjacent to the first elastic sub-assembly, are adjacent to one another and are configured to be abutted against each other after bending, to restrict a further bending of the first and second elastic strips.

2. The orthopedics restoration fixation device of claim 1, wherein the adjustment assembly comprises:
    a first adjustment member fixedly connected to the first clamping assembly;
    a second adjustment member fixedly connected to the second clamping assembly; and
    an operation sub-assembly being in a drive connection with the first adjustment member and the second adjustment member, so that the operation sub-assembly drives, by the first adjustment member and the second adjustment member, respectively, the first clamping assembly and the second clamping assembly to move towards each other or away from each other.

3. The orthopedics restoration fixation device of claim 2, wherein:

the first adjustment member comprises a first screw rod;
the second adjustment member comprises a second screw rod;
the operation sub-assembly comprises a first rotation shaft rotatably provided on the first base; and
a first bevel gear and an operation part are respectively provided at first and second ends of the first rotation shaft, the first screw rod and the second screw rod are coaxially provided, a second bevel gear and a third bevel gear are respectively provided at ends of the first screw rod and the second screw rod facing towards each other, and the first bevel gear is engaged respectively with the second bevel gear and the third bevel gear.

4. The orthopedics restoration fixation device of claim 1, wherein:
the first clamping assembly comprises:
a first clamping member; and
a first support member connected to the first clamping member and movably provided on the first base; and
the second clamping assembly comprises:
a second clamping member provided opposite to the first clamping member; and
a second support member connected to the second clamping member and movably provided on the first base.

5. The orthopedics restoration fixation device of claim 4, wherein the first clamping member and the second clamping member are arc-shaped clamping members, and concave surfaces of the first clamping member and the second clamping member face towards each other and are respectively provided with a first anti-slip mat and a second anti-slip pad.

6. The orthopedics restoration fixation device of claim 1, wherein:
the second base is connected to the first base, and the third base is located at a side of the second base away from the first base; and
a relative movement direction between the second base and the third base is substantially perpendicular to a relative movement direction between the first clamping assembly and the second clamping assembly.

7. The orthopedics restoration fixation device of claim 6, wherein a first sleeve is provided on a first one of the second base and the third base, a positioning rod is provided on a second one of the second base and the third base, and the positioning rod is provided to pass through the first sleeve and be movable in an axial direction of the first sleeve.

8. The orthopedics restoration fixation device of claim 7, wherein a second spring is sleeved on the positioning rod, and has two ends respectively abutted against the second one of the second base and the third base and the first sleeve.

9. The orthopedics restoration fixation device of claim 1, wherein:
first springs are provided respectively between the elastic ball and the second base and between the elastic ball and the third base.

10. The orthopedics restoration fixation device of claim 9, wherein each of the first springs is provided within a guide sleeve of which a first end is fixedly connected to the second base or the third base and a second end is close to the elastic ball.

11. The orthopedics restoration fixation device of claim 1, wherein:
a plurality of said elastic sub-assemblies are provided at intervals between the second base and the third base;
each of the elastic sub-assemblies comprises: one said elastic ball, and two said elastic strips opposite to each other.

12. The orthopedics restoration fixation device of claim 1, wherein the clamping mechanism is detachably connected to the shock absorbing mechanism.

13. The orthopedics restoration fixation device of claim 12, wherein a block is provided on the first base, a groove is formed in the shock absorbing mechanism, and the block is configured to be fitted into the groove by rotation.

14. The orthopedics restoration fixation device of claim 1, further comprising an anti-slip mat layer provided between the supporting rod and the second sleeve.

15. The orthopedics restoration fixation device of claim 1, further comprising a positioning roll provided at one end of the slider and abutted against the inclined guide rail.

* * * * *